United States Patent
Wieters et al.

(10) Patent No.: US 12,245,744 B2
(45) Date of Patent: Mar. 11, 2025

(54) ENDOSCOPE

(71) Applicant: OLYMPUS WINTER & IBE GMBH, Hamburg (DE)

(72) Inventors: Martin Wieters, Barsbuettel (DE); Annika Goehring, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 633 days.

(21) Appl. No.: 17/438,162

(22) PCT Filed: Feb. 27, 2020

(86) PCT No.: PCT/EP2020/055202
§ 371 (c)(1),
(2) Date: Sep. 10, 2021

(87) PCT Pub. No.: WO2020/182485
PCT Pub. Date: Sep. 17, 2020

(65) Prior Publication Data
US 2022/0142459 A1    May 12, 2022

(30) Foreign Application Priority Data
Mar. 13, 2019  (DE) .......................... 102019106453.8

(51) Int. Cl.
A61B 1/00  (2006.01)
A61B 1/05  (2006.01)
G02B 23/24  (2006.01)

(52) U.S. Cl.
CPC ...... *A61B 1/00096* (2013.01); *A61B 1/00179* (2013.01); *A61B 1/05* (2013.01); *G02B 23/2476* (2013.01)

(58) Field of Classification Search
CPC ... A61B 1/00096; A61B 1/00179; A61B 1/05; A61B 1/00163; A61B 1/00174;
(Continued)

(56) References Cited

U.S. PATENT DOCUMENTS

| 4,727,859 A | 3/1988 | Lia |
| 2012/0182458 A1* | 7/2012 | Ishii ........................ G03B 17/17 359/833 |

(Continued)

FOREIGN PATENT DOCUMENTS

| DE | 102014202669 A1 | 8/2015 |
| DE | 102017122279 A1 | 3/2019 |

(Continued)

OTHER PUBLICATIONS

International Search Report dated Jun. 18, 2020 issued in PCT/EP2020/055202.
(Continued)

*Primary Examiner* — Ryan N Henderson
*Assistant Examiner* — Timothy Tuan Luu
(74) *Attorney, Agent, or Firm* — Scully, Scott, Murphy & Presser, P.C.

(57) ABSTRACT

An endoscope including: an elongated shaft and an optical system disposed in the shaft. The optical system includes at least one prism. The prism is mounted in a prism holder. The prism holder having first and second stops for aligning the prism in at least first and second directions, respectively. Wherein the first stop forms a planar stop surface against which a first planar surface of the prism rests, and the second stop forms a linear stop contour against which a second planar surface of the prism rests.

6 Claims, 3 Drawing Sheets

(58) Field of Classification Search
CPC ............ A61B 1/00181; A61B 1/00013; G02B 23/2476; G02B 7/1805; G02B 23/24; G02B 23/2407; G02B 23/2415; G02B 23/2423; G02B 23/243; G02B 23/2438; G02B 23/2446; G02B 23/2453
See application file for complete search history.

(56) References Cited

U.S. PATENT DOCUMENTS

| | | |
|---|---|---|
| 2016/0213236 A1 | 7/2016 | Hruska et al. |
| 2016/0345805 A1 | 12/2016 | Wieters et al. |
| 2020/0225446 A1 | 7/2020 | Wieters |

FOREIGN PATENT DOCUMENTS

| | | | | |
|---|---|---|---|---|
| JP | 2007094359 A | * | 4/2007 | |
| WO | WO-2013069335 A1 | * | 5/2013 | ......... A61B 1/00096 |
| WO | WO-2016075997 A1 | * | 5/2016 | ............... A61B 1/00 |
| WO | WO-2017086298 A1 | * | 5/2017 | ......... A61B 1/00096 |

OTHER PUBLICATIONS

Written Opinion dated Jun. 18, 2020 issued in PCT/EP2020/055202.
German Office Action dated Oct. 1, 2020 issued in DE 102019106453.8.

* cited by examiner

ENDOSCOPE

CROSS-REFERENCE TO RELATED APPLICATION

The present application is based upon and claims the benefit of priority from PCT/EP2020/055202 filed on Feb. 27, 2020, which claims priority to DE 10 2019 106 453.8 filed on Mar. 13, 2019, the entire contents of each of which is incorporated herein by reference.

BACKGROUND

Field

The present disclosure relates to an endoscope and more particularly to an endoscope having an elongated shaft and an optical system disposed in the shaft, wherein the optical system comprises at least one prism, and wherein the prism is mounted in a prism holder which has stops in at least two main directions for aligning the prism.

Prior Art

Endoscopes have long been used in medicine to examine and/or treat cavities in the body of a human or animal patient that are difficult to access. In engineering, endoscopes are used to inspect cavities that are difficult to access, for example, in technical systems.

Endoscopes have an elongated shaft with an optical system disposed therein. Depending on the intended application, the shaft may be rigid or flexible. An optical system, which comprises an objective lens at the distal end of the shaft, is routinely arranged in the shaft.

An image captured by the objective lens is either converted by an electronic image converter into video signals, which are transmitted by electrical lines or wirelessly to an image processing device, or the image is transmitted by an optical image guide to an eyepiece at the proximal end of the endoscope, where it can be viewed by the naked eye or by means of a video camera.

In the simplest case, a beam path of the optical system passes through the entire optical system straight and parallel to a longitudinal axis of the endoscope shaft. However, it is often necessary to deflect the beam path in the optical system from a first direction to a second direction, for example to provide an endoscope with oblique viewing optics, or to make the placement of an electronic image converter in the endoscope more convenient. In these cases, one or more prisms are usually used to deflect the beam path. In some situations, it may also be necessary to guide the beam path of an optical system through an optical element with plane-parallel entrance and exit surfaces. Such an optical element is also considered a prism for the purposes of the invention described below.

For the imaging quality of the endoscope, an accurate and stable alignment of each prism is required. This is commonly ensured by mounting a prism in a mechanical prism holder, which comprises stops for the prism in at least two main directions. The stops are usually plane stop surfaces against which the prism rests with corresponding planar surfaces.

A corresponding endoscope is described in DE 10 2017 122 279 A1 of the applicant, which has not been pre-published.

When using two stop surfaces, however, the problem arises that the positioning of the prism in the two main directions is mechanically overdetermined. The prism will only be able to rest fully against the two stop surfaces if the angle between the contact surfaces exactly matches the corresponding angle between the planar surfaces of the prism. If, on the other hand, the angles do not coincide exactly, incomplete contact of the prism occurs on one of the two stop surfaces, which on the one hand may lead to inaccurate positioning, and on the other hand may result in high surface pressures between the prism and the prism holder, which in the worst case may damage or even destroy the prism.

SUMMARY

It is therefore an object to provide an endoscope which is improved with respect to the problems described.

Such object can be achieved by an endoscope with an elongated shaft and an optical system disposed in the shaft, wherein the optical system comprises at least one prism, and wherein the prism is mounted in a prism holder which has stops in at least two main directions for aligning the prism, which is further configured in that a first stop forms a planar stop surface against which a first planar surface of the prism rests, and in that a second stop forms a linear stop contour against which a second planar surface of the prism rests.

The configuration of the second stop as a linear stop contour eliminates the mechanical overdetermination of the stops. The prism thus always rests with its first planar surface against the planar stop surface, while the second planar surface rests against the linear stop contour.

Assuming that the linear stop contour is not exactly perpendicular to the plane stop surface, the position of the prism is fixed by the described stops with respect to three rotational degrees of freedom and two translational degrees of freedom without overdetermination.

The translatory determination along a third main direction may be made by a further stop. In many cases, however, a corresponding determination may be dispensable, namely if the third main direction runs parallel to an optical axis of the optical system along which further optical components must be longitudinally adjusted. The further optical components may be, for example, lenses of the objective lens.

In a further embodiment of an endoscope, the linear stop contour of the second stop may be approximately parallel to the stop surface of the first stop. The linear stop contour is then approximately parallel to the stop surface of the first stop when the angle between the linear stop contour and a surface normal of the stop surface is approximately 90°. For example, this may include angles that are between 70° and 110°, such as between 80° and 100°. A corresponding alignment of the linear stop contour enables a particularly secure contact of the prism.

In another embodiment of an endoscope, the average distance of the linear stop contour of the second stop to the stop surface of the first stop may correspond approximately to half the extension of the prism in a direction perpendicular to the stop surface of the first stop. The prism is thus supported at approximately half its height above the plane stop surface, making the mounting particularly stable. At the same time, the influence of angular tolerances of the plane stop surface on the positioning of the prism is minimized by the corresponding arrangement of the linear stop contour.

According to another embodiment of an endoscope, the second stop may have a cylindrical surface at least in sections, and the linear stop contour may correspond to a surface line of the cylindrical surface. The corresponding embodiment simultaneously achieves a linear contact between the prism and the linear stop contour and a defined surface pressure, which is determined by the radius of the cylindrical surface. This counteracts damage to the prism caused by uncontrollably high surface pressures.

In a further embodiment of an endoscope, the prism holder may have pressing elements which press the prism in the direction of the stops. The pressing elements may be, for example, balls or ball-like bodies made of metal, glass or ceramic, which are guided through channels in the prism holder to the prism and are fixed there by suitable means, this may include, for example, bonding.

The pressing elements can act on surfaces of the prism which are opposite the planar surfaces of the prism with which the prism rests against the stops. Thus, in an endoscope according to another embodiment, a first pressing element may act on a surface of the prism which is opposite to the first planar surface of the prism. Alternatively or additionally, a second pressing element may act on a surface of the prism which is opposite to the second planar surface. In this way, the pressing elements secure the prism against displacement in the prism holder.

In another embodiment of an endoscope, the line of action of a pressing force exerted by the second pressing element on the prism may intersect the linear stop contour of the second stop or pass it at a distance which is less than 0.1 times the extension of the prism in the direction of the line of action. This embodiment avoids the action of shear forces and/or tilting moments on the prism.

In another embodiment of an endoscope, the first planar surface of the prism may form an exit surface for the beam path of the optical system, and an electronic image converter may be disposed proximate to the first planar surface of the prism. In this way, the length of an optical path between the exit surface of the prism and the electronic image converter may be specified with particular certainty. Thereby, the first stop may comprise a recess in which the electronic image converter is disposed.

BRIEF DESCRIPTION OF THE DRAWINGS

The embodiments will be explained in more detail below with reference to a number of figures, the embodiments shown in the figures being intended merely to provide a better understanding of the invention without limiting it, in which.

DETAILED DESCRIPTION

Figure 1:
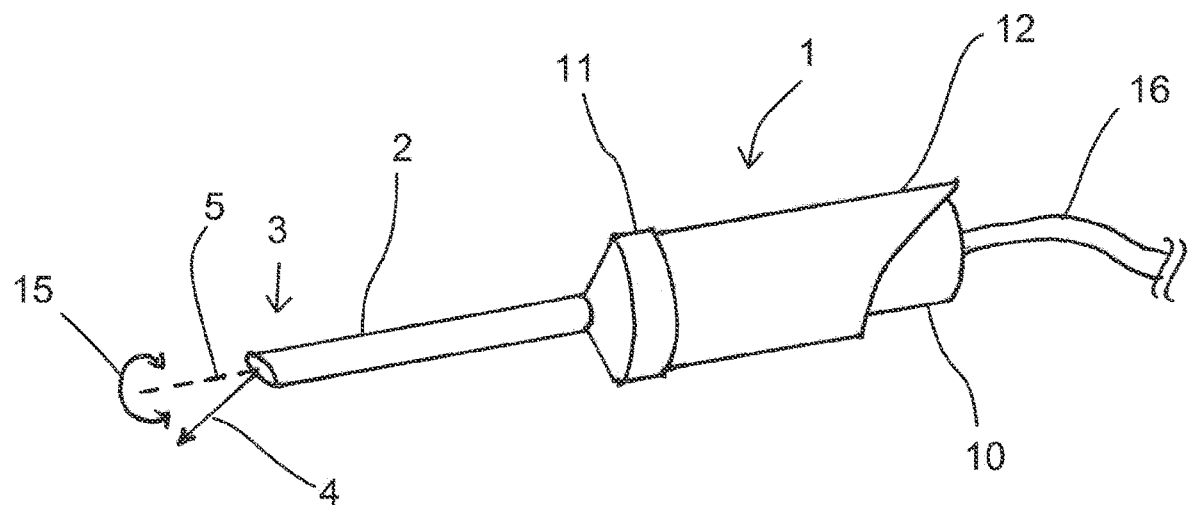
FIG. 1 illustrates an endoscope.

FIG. 1 shows an endoscope 1, in this case a video endoscope, with an elongated shaft 2, in the distal end of which an optical system in the form of an objective lens 3 is disposed. The objective lens 3 may have a lateral viewing direction, i.e., a viewing direction of the objective lens 3 indicated by the arrow 4 deviates from a longitudinal axis 5 of the video endoscope 1.

Furthermore, the endoscope 1 comprises a main body 10 at which a first handle element 11 and a second handle element 12 are disposed.

The first handle element 11 is configured as a rotary wheel at the distal end of the main body. By means of the first handle element 11, the shaft 2, the objective lens 3, and the main body 10 can be rotated around the longitudinal axis 5 of the endoscope, so that the viewing direction of the video endoscope also rotates around the longitudinal axis 5 of the video endoscope. This is indicated by the double arrow 15.

An electronic image converter (not shown) is disposed in the shaft 2 proximally of the objective lens 3, for example a CCD chip or a CMOS chip. Of course, several image converters may also be provided to image different color channels or partial images of stereo optics. The electronic image converter converts the image projected by the objective lens 3 into electrical signals, which are transmitted through the shaft 2 into the main body 10 and from there via a cable 16 to an external processing device (not shown). The processing device may process the electrical signals, for example, for display on a monitor or for storage in a memory element.

In order to keep the horizontal position of the video image constant when the viewing direction of the endoscope 1 is rotated, the image converter is rotatably arranged in the shaft 2, and is rotationally coupled to the second handle element 12. For this purpose, a magnetic coupling acting through the shaft or through the wall of the main body 10 is provided. The structure of this magnetic coupling is known per se and need not be explained in detail here.

The second handle element 12 is rotatably arranged relative to the first rotary body 11 and the main body 10. If the viewing direction of the endoscope is now rotated by rotating the first handle element 11, the second handle element 12 can be held in place at the same time, whereby the orientation of the electronic image converter also remains constant.

If the endoscope 1 has a straight viewing direction, i.e., the viewing direction is parallel to the longitudinal axis 5, the two handle elements 11 and 12 may be omitted, since the endoscope 1 can then simply be held on the main body 10 and a rotational movement is not required.

Figure 2:
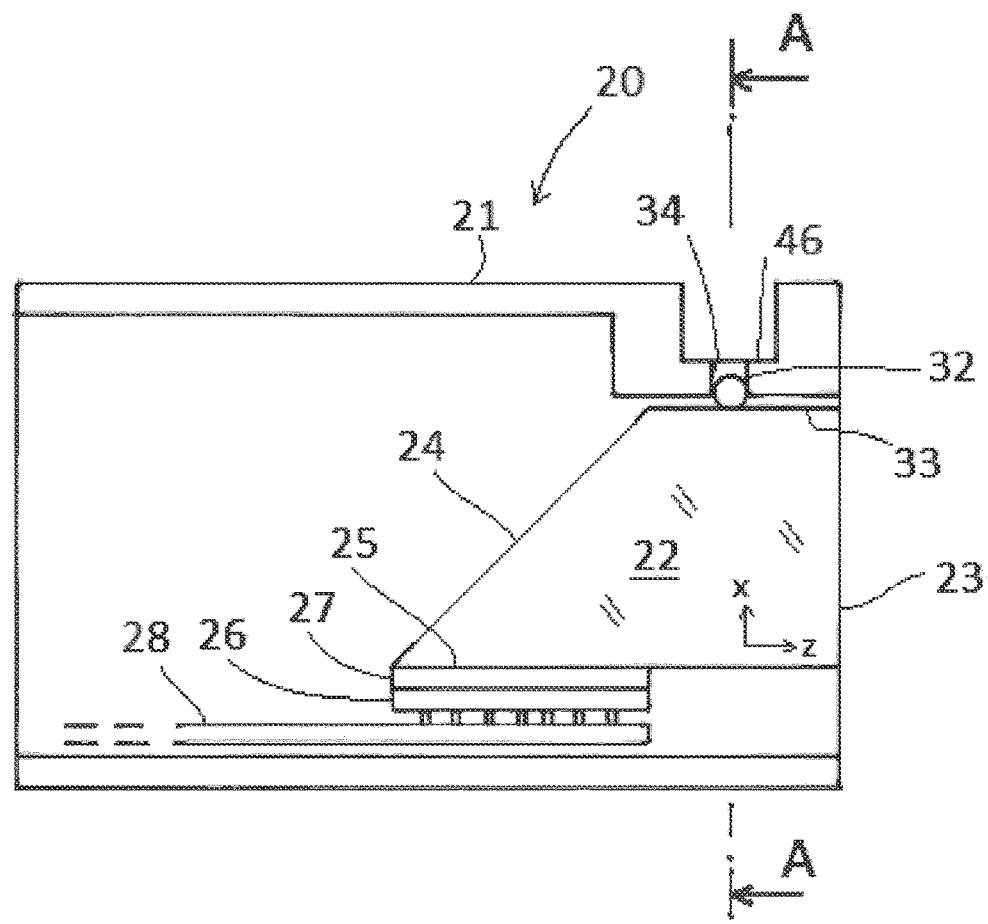
FIG. 2 illustrates a prism holder of an endoscope in longitudinal section.
Figure 3:
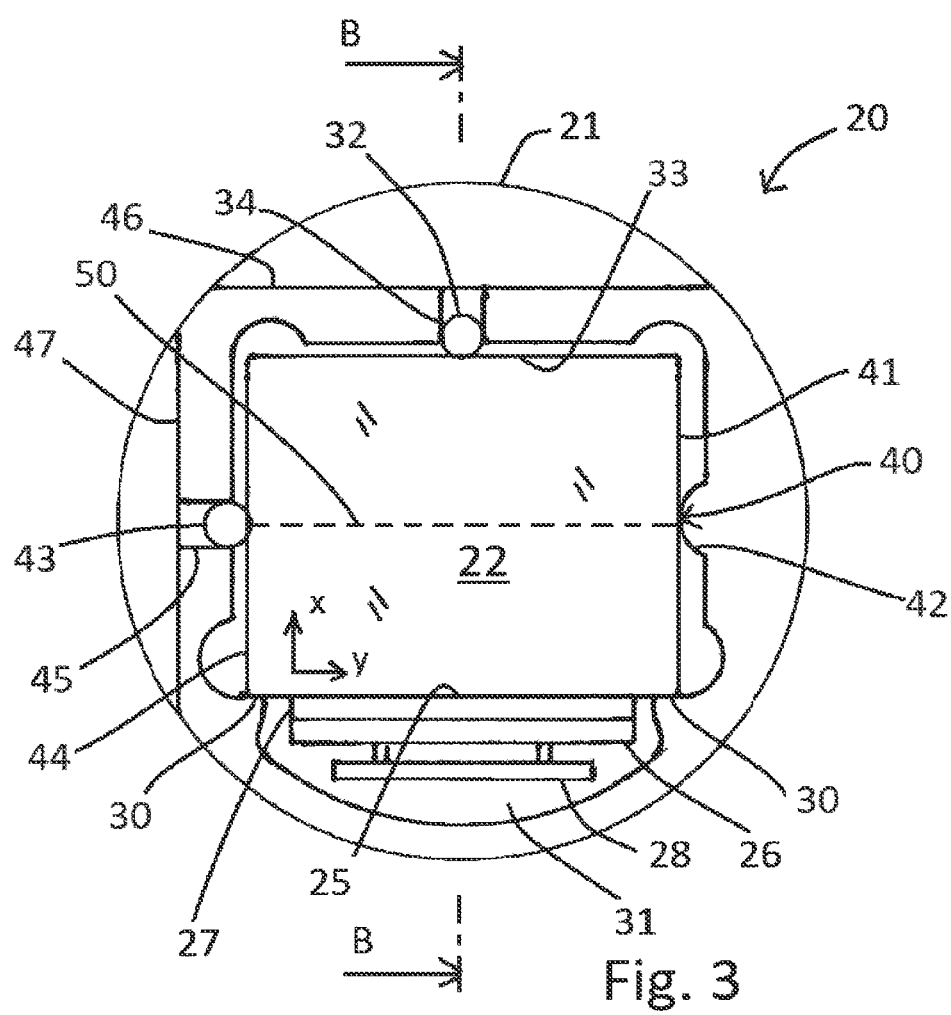
FIG. 3 illustrates a prism holder of an endoscope in cross section.

FIGS. 2 and 3 show a prism holder 20 which is part of an optical system of the endoscope 1. Here, FIG. 2 shows a section along the line B-B in FIG. 3, and FIG. 3 shows a section along the line A-A of FIG. 2.

The prism holder 20 comprises a substantially cylindrical sleeve 21 in which a prism 22 is received. In the present example, the prism serves to deflect a beam of rays entering an entrance surface 23 by 90° at a reflection surface 24 and to guide it to an exit surface 25.

An electronic image converter 26 is disposed at the exit surface 25 of the prism 22. An optical filter element 27 may be provided between the exit surface 25 and the image converter 26, which may comprise, for example, an IR cutoff filter or a Moiré filter. The image converter 26 is supplied via an electrical connection element 28, via which video signals generated by the image converter 26 are also discharged. The connection element 28 may comprise a flexible circuit board.

For a clean optical image, the prism 22 must be aligned translationally and rotationally in the main x, y, z directions. Here, if necessary, a translational alignment in one main direction, e.g., the main direction z, can be omitted if this main direction is parallel to an optical axis of the optical system 3, and the optical system is adjusted separately in this main direction.

For alignment of the prism 22, the prism holder 20 has a first stop formed by a plane stop surface 30. The stop surface 30 has a recess 31 in which the image converter 26 is arranged.

The prism 22 rests with the exit surface 25, which is a planar surface, against the stop surface 30, thereby fixing the prism with respect to a translation along the main direction x and with respect to a rotation about the main directions y and z.

A pressing element in the form of a pressing ball 32 presses on a surface 33 of the prism 22 opposite to the exit surface 25 and thus holds it in firm contact with the stop surface 30. The pressing ball 32 is inserted into a channel 34 of the sleeve 21 and can be fixed there, for example by means of an adhesive. The adhesive is not shown for clarity. Instead of the pressing ball 32, other pressing elements may also be used, for example a spring or a screw.

In order to fix the prism 22 with respect to a translation in the main direction y and a rotation about the main direction x, another stop surface could be provided which is perpendicular to the main direction x. However, such a stop surface would also cause an additional fixation with respect to a rotation about the main direction z, thus the position of the prism 22 would be overdetermined. Therefore, instead of another stop surface, a linear stop contour 40 is provided, which can be seen in FIG. 3 as a point of contact between a lateral planar surface 41 of the prism 22 and the second stop 42. The linear stop contour 40 is only visible here as a point, since it runs perpendicular to the drawing plane of FIG. 3. The linear stop contour 40 is thus parallel to the stop surface 30 and perpendicular to the main direction x, although certain angular deviations, for example by up to +/−10°, or by up to +/−20°, can be tolerated.

The linear stop contour 40 fixes the prism 22 with respect to a translation in the main direction y and with respect to a rotation about the main direction x, without causing a further fixation with respect to a rotation about the main direction z. Thus, there is no overdetermination here.

A pressing element in the form of a pressing ball 43 presses on a surface 44 of the prism 22 opposite to the planar surface 41 and thus holds the prism 22 in firm contact with the linear stop contour 40. The pressing ball 43 is inserted into a channel 45 of the sleeve 21 and can be fixed there, for example by means of an adhesive which is also not shown. Instead of the pressing ball 43, other pressing elements can also be used, for example a spring or a screw.

The second stop 42 has a cylindrical outer contour in the region of the linear stop contour 40, the linear stop contour 40 being a surface line of the cylindrical contour. This limits a surface pressure between the planar surface 41 and the second stop 42.

The distance of the linear stop contour 40 from the stop surface 30 corresponds approximately to half the extension of the prism in the main direction x, thereby achieving a particularly stable contact of the prism 22. At the same time, a line of action 50 of the pressure ball 42 on the prism 22 runs in such a way that it intersects the linear stop contour 40 or passes it at a distance which is smaller than 0.1 times the extension of the prism 22 in the direction of the line of action 50. This reduces tilting moments and shear forces on the prism 22 as far as possible.

For easier placement of the pressure balls 32, 43, the sleeve 21 has flats 46, 47.

Figure 4:
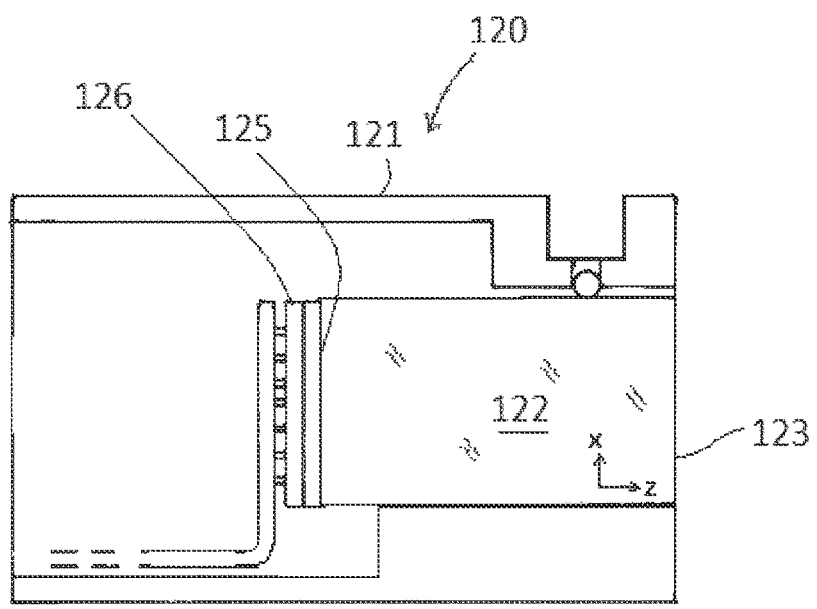
FIG. 4 illustrates another prism holder of an endoscope in longitudinal section.

FIG. 4 shows another prism holder 120 of an endoscope in longitudinal section.

The prism holder 120 again comprises a substantially cylindrical sleeve 121 in which a prism 122 is received. In the present example, the prism serves to guide a beam of radiation entering an entrance surface 123 to an exit surface 125 without deflection.

An electronic image converter 126 is in turn disposed at the exit surface 125 of the prism 122. The structure of the image converter 126 and the orientation of the prism 122 along the main directions x and y correspond to the solutions shown in FIGS. 2 and 3 for the prism holder 20.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscope comprising:
   an elongated shaft; and
   an optical system disposed in the shaft, the optical system comprises at least one prism, and the prism is mounted in a prism holder, the prism holder having first and second stops for aligning the prism in at least first and second directions, respectively,
   wherein the first stop forms a planar stop surface against which a first planar surface of the prism rests, and
   the second stop forms a linear stop contour against which a second planar surface of the prism rests;
   the prism holder has first and second pressing elements disposed in first and second cavities formed in first and second walls, respectively, the first and second pressing elements are separate from the first and second stops, the first and second pressing elements project from the first and second walls in the first and second directions, respectively, to press the prism in the first and second directions towards the first and second stops;
   the first pressing element acts on a first surface of the prism which opposes the first planar surface of the prism;
   the second pressing element acts on a second surface of the prism which opposes the second planar surface of the prism; and
   a line of action of a pressing force exerted by the second pressing element on the prism intersects the linear stop contour of the second stop or passes it at a distance which is less than 0.1 times the extension of the prism in a direction of the line of action.

2. The endoscope according to claim 1, wherein the linear stop contour of the second stop is approximately parallel to the planar stop surface of the first stop.

3. The endoscope according to claim 1, wherein an average distance of the linear stop contour of the second stop to the planar stop surface of the first stop corresponds approximately to half an extension of the prism in a direction perpendicular to the planar stop surface of the first stop.

4. The endoscope according to claim 1, wherein the second stop has a cylindrical surface at least in sections, and the linear stop contour corresponds to a surface line of the cylindrical surface.

5. The endoscope according to claim 1, wherein the first planar surface of the prism forms an exit surface for the beam path of the optical system, and an electronic image sensor is disposed proximate to the first planar surface of the prism.

6. The endoscope according to claim 5, wherein the first stop has a recess in which the electronic image sensor is disposed.

* * * * *